United States Patent [19]

Geho et al.

[11] Patent Number: 4,501,728

[45] Date of Patent: Feb. 26, 1985

[54] MASKING OF LIPOSOMES FROM RES RECOGNITION

[75] Inventors: W. Blair Geho; John R. Lau, both of Wooster, Ohio

[73] Assignee: Technology Unlimited, Inc., Wooster, Ohio

[21] Appl. No.: 456,269

[22] Filed: Jan. 6, 1983

[51] Int. Cl.³ .................... A61K 9/50; A61K 9/42; A61K 37/22

[52] U.S. Cl. .................... 424/38; 424/31; 424/19; 428/402.2; 264/4.6; 436/829

[58] Field of Search .................... 424/38, 31, 9, 19; 428/402.2; 436/829; 264/4.6

[56] References Cited

U.S. PATENT DOCUMENTS

| | | | |
|---|---|---|---|
| 3,499,962 | 3/1970 | Wurzberg | 264/4.6 X |
| 3,960,757 | 6/1976 | Morishita | 424/38 X |
| 3,993,747 | 11/1976 | Gaffar | 424/88 |
| 4,010,251 | 3/1977 | Green | 424/1.1 |
| 4,013,507 | 3/1977 | Rembaum | 195/1.8 |
| 4,116,776 | 9/1978 | Dalbow | 195/103.7 |
| 4,187,194 | 2/1980 | Wellman | 264/4.6 X |
| 4,193,983 | 3/1980 | Ullman | 424/38 X |
| 4,224,179 | 9/1980 | Schneider | 428/402.2 X |
| 4,225,487 | 9/1980 | Cuatrecasas | 424/92 |

OTHER PUBLICATIONS

Morell, et al., Jour. Biol. Chem., vol. 246, No. 5, Mar. 10, pp. 1461–1467, 1971, "Role of Sialic . . . ".

Primary Examiner—Richard D. Lovering
Assistant Examiner—Catherine S. Kilby
Attorney, Agent, or Firm—Frijouf, Rust & Pyle

[57] ABSTRACT

A biochemical membrane covered with sialic residues thereby provides a coating that masks the surface membrane from recognition and removal by the scavenging RES cells of the body.

4 Claims, 3 Drawing Figures

BIPOLAR LIPID MEMBRANE STRUCTURE

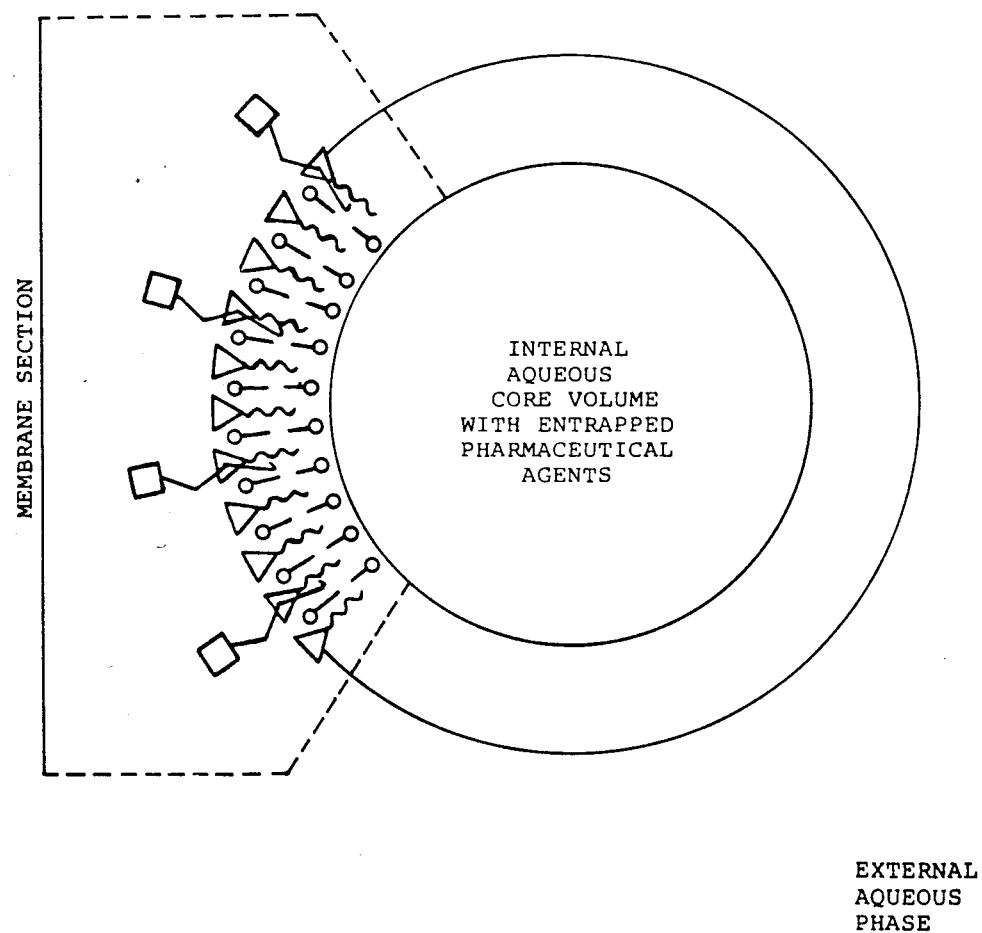

MASKING OF LIPOSOMES FROM RES RECOGNITION

BACKGROUND OF THE INVENTION

The ability of liposomes to encapsulate pharmacological agents thereby sequestering them from the surrounding medium, together with their potential for site-specific delivery in vivo, has stimulated interest in their use as drug carriers for enhancing therapeutic index.

Intravenously administered liposomes generally become associated with organs of the reticuloendothelial system, mainly the liver and spleen, a distribution shared with other intravenously injected colloids and suspensions. This tendency restricts the ability of liposomes to be directed to specific target tissues.

Liposomes were first produced in England in 1965 according to the July/August 1981 issue of Prospectus. They are easily made in the laboratory from common, low cost material such as egg lecithin.

The literature is replete with reports of studies directed to attempts to target the liposomes to a specific cell or organ, in order to avoid having the medication taken up by the entire system. However, only a very few reports of actual success to limited systems are known. One specific example of success was reported at a California conference on new medical technology sponsored by Robert S. First, Inc., White Plains, N.Y. It was reported that treatment of tropical parasitic disease Leishmaniasis is based on derivatives of antimony. The problem is that doses of antimony strong enough to kill the parasite may also kill the patient.

Liposomes technology provides a novel treatment of the disease for two simple reasons. First, it is known that the parasite is found entirely in the cells that make up one branch of the immune system known as the reticuloendothelial system which will hereafter be referred to as RES. Secondly, liposomes injected intravenously are cleared from the blood by these varied RES cells. In one experiment, liposomes were loaded with an antimony compound and injected into rats that had been infected with the parasite. Examination of the rats livers revealed that drugs delivered via the liposomes totally destroyed the parasites.

This success is due to the fact that the RES recognizes liposomes and by taking the liposomes from the blood system and dismantling the lipid cover, exposes the very infected areas to strong doses of the antimony compounds which could not be tolerated in the entire system.

It is important to note that the reticuloendothelial system may inhibit efforts to use liposomes for treatment because the RES will scavenge the liposomes.

Therefore, it is an object of this invention to produce a liposome which is masked from recognition by the RES.

Another object of the invention is to produce a biochemical membrane covered with sialic acid residues thereby providing a coating that masks the surface of the membrane from recognition by the scavenging cells of the body much like the surface of a red blood cell is masked from scavenging cell recognition and uptake during its circulating lifetime.

SUMMARY OF THE INVENTION

This invention is embodied by the product of a procedure of coating the external surface of a carrier system with sialic acid residues to mask the surface of the carrier from recognition by the scavenging cells of the animal body.

BRIEF DESCRIPTION OF THE DRAWINGS

FIG. 3 is the final embodiment of the invention whereby the bipolar lipid membrane structure such as a vesicle is surface masked by the embedding of the hydrophobic portion, bracket A, of FIG. 1 into the lipid surface of the vesicle and projecting the head or hydrophilic portion, bracket B, of the molecule illustrated in FIG. 1 from the vesicle surface.

DETAILED DESCRIPTION

Figure 1:
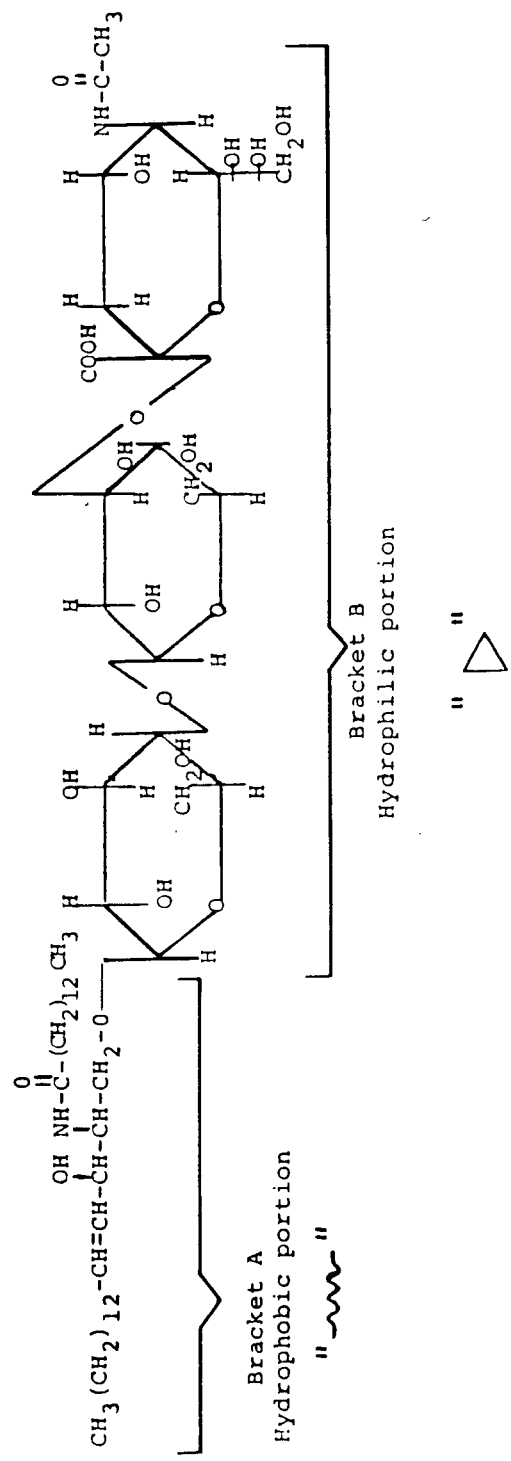
FIG. 1 is an example of a structure which could be employed to produce a coating of sialic acid residues on the surface of a biochemical membrane.

An important prerequisite for the success in the overall application of pharmacologically active agents is specificity. A targeted lipid vesicle as in FIG. 2 should fulfill this requirement since it consists of a bipolar lipid membrane that envelops an aqueous core volume and can serve as a biologically targeted carrier for pharmacologically active agents such as drugs, hormones and diagnostics. Until now the general consensus among the drug delivery practitioners has been that once the appropriate targeting molecule is selected, it is then a matter of properly incorporating this molecule into the bipolar lipid membrane structure of the vesicle so that the target molecule can be recognized by the appropriate cellular receptor.

The scientific literature in the vesicle drug delivery area is replete with benefits derived from targeted vesicle drug delivery systems. However, to date there is no known vesicle drug delivery system in the pharmaceutical marketplace.

It has been discovered that the primary problem in this area of drug delivery resides in the fact that targeted vesicles have particular lipid membrane characteristics that permit them to be recognized as foreign entities by the scavenging organs of the body such as the liver, spleen and lungs. As a consequence, they are removed from the circulatory system before they have had an opportunity to be selectively targeted to the appropriate cell-type and perform their designated function.

This invention addresses the above problem and describes an entirely new and unique drug delivery system to deliver pharmacological agents to their proper sites of action.

This invention is embodied by the product of a procedure, or process, or method of coating or covering the external surface of a synthetic carrier system with sialic acid residues as illustrated in FIG. 3.

An embodiment of this invention may be synthesized by constructing a biochemical membrane that is covered with sialic acid residues. These sialic acid residues provide a unique coating that masks the surface of the membrane from recognition by the scavenging cells of the body thereby allowing the membrane to survive and circulate systemically for an indefinite period of time. For drug delivery purposes, it is necessary that the membrane envelop an interior aqueous core volume so that it is capable of entrapping drugs and pharmaceutical agents. The vesicle has a chemical composition resulting from sialic acid residues on exterior surfaces of the membrane that differs significantly from the composition of the traditional array of drug carrier systems. Thus, the vesicle not only has a totally different chemical composition which results in new and unique properties, but also is capable of performing different and specialized functions in biological systems. One example of this function is the evasion of the scavenging cells of the body so as to permit it to circulate throughout the system.

The vesicle system of circulation can best be compared to natural red cells that circulate in the body. Red blood cells evade the scavenging organs for a prolonged period of time (120 days) because they have a sialic acid outer layer. The red blood cells then deteriorate and lose their sialic acid coating on the outer layer. The exposed galactose residues are then recognized by the Ashwell receptors of the liver and the spent cells are removed. The vesicle of the invention may have a similar useful life span. Then, due to the action of endogenous neuramindase which is present in the body, the sialic acid sloughs off exposing galactose residues. The galactose is then recognizable by the liver which will then take the vesicles in and dispose of them in a natural fashion.

There are two important kinds of vesicles, according to this invention, that result in a diversification and broadening of previous drug delivery capabilities. The first kind of vesicle has a membrane that is *permeable* with respect to the entrapped pharmacological agent. This membrane is designed and synthesized so that it permits delivery of the pharmacological agent into the circulatory system in a regulated manner. Hence this type of vesicle would be classified as belonging to a circulating non-targeted time-release drug delivery system. The vesicle would be eventually removed from the system circulation by the endogenous action of the enzyme neuramindase after the unique mask provided by this invention has degenerated.

The second kind of vesicle is synthesized with an *impermeable* membrane with respect to the entrapped pharmacological agent and whose surface has been altered by the addition of sialic acid residues, according to this invention. In addition to masking the surface of these vesicles with sialic acid residues, a specific targeting molecule is introduced thereby creating a targeting vesicle which can deliver its cargo to the appropriate site of action. The sialic acid coating masks foreign membrane constituents and permits the vesicles to remain in circulation until the targeting molecules have directed the carrier to the appropriate site of action.

It is assumed that the reader is informed in the technique of manufacturing liposomes which also are referred to as vesicles. If not, reference is made to the following publications: *The New England Journal of Medicine,* Sept. 23, 1976, page 704; G. Weissmann et al, *Proceedings of the National Academy of Science, U.S.A.,* Volume 74, pp. 88-92 (1975); *Journal of Biological Chemistry,* Volume 245, pp. 3295-3301, 1970; *Nature,* Volume 240, pp. 167-172 (1972); *Journal of Clinical Investigation,* Volume 53, pp. 536-543 (1974).

Figure 2:
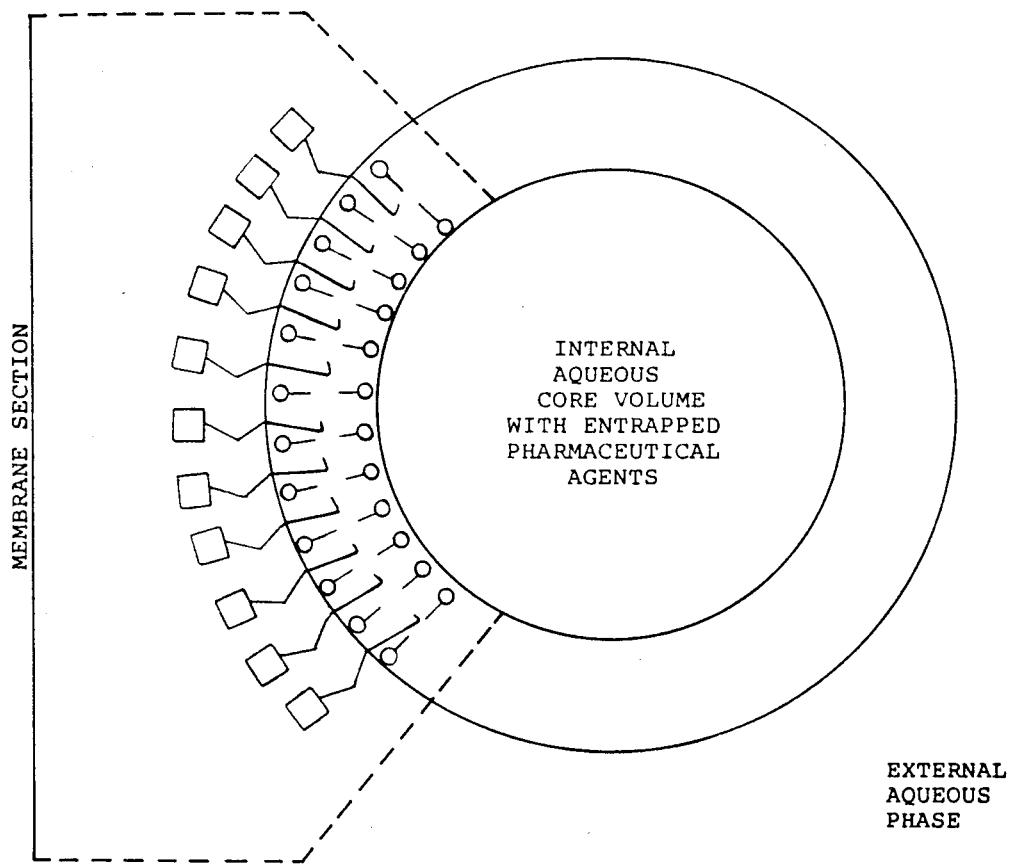
FIG. 2 is a bipolar lipid membrane structure such as a vesicle having targeting molecules for directing the vesicle to a receptor cell and spaces between the targeting molecules unmasked on the surface of the membrane.

In FIG. 2, a section of a double ring illustration is used as an accepted means for illustrating and discussing liposomes and vesicles. The symbol "O—" is an amphiphilic molecule where "O" represents the hydrophilic portion that is exposed to the aqueous media in which the vesicle is manufactured, and where "—" represents the hydrophobic (lipophilic) portion that is buried in the interior of the membrane. These molecules form the basic structures of the vesicle.

The symbol "☐⌒" is a targeting molecule where "☐⌒" represents the hydrophilic portion that is exposed to the aqueous media in which the vesicle resides during manufacture and where " " represents the hydrophobic portion that is buried in the interior of the membrane.

Note that in FIG. 2 that there is a large exposed surface between the targeting molecule that is recognized by the RES and therefore removed from the system very quickly.

This invention is embodied in the means for preventing the recognition of the vesicle and is illustrated in FIG. 3. The elements referred to in FIG. 2 are repeated and the molecule of this invention used to mask the surface is illustrated by the symbol "▷⌒" which is an amphiphilic structure illustrated in FIG. 1 that coats and changes the membrane structure masking its recognition by the scavenging cells. The triangle "▷" is the hydrophilic portion and the "⌒" represents the hydrophobic portion.

FIG. 1 is an example of a structure which could be employed to produce a coating of sialic acid residues on the surface of a biochemical membrane. These structures are complex glycosphingolipids composed of sphingosine, fatty acid, one or more sugars and characteristically N-acetylneuraminic acid. An example of such a structure contains equimolar amounts of sphingosine, fatty acid, glucose, galactose and N-acetylneuraminic acid (sialic acid).

The bracket A is a tail or hydrophobic portion and the bracket B is a head or hydrophilic portion.

When this compound of FIG. 1 is incorporated in the bipolar vesicle membrane during vesicle manufacture, it will assume the protective position as illustrated in FIG. 3.

It has been found that vesicles manufactured with the protective masking molecule as thus described and illustrated, will remain in the blood for a prolonged period of time if not provided with a targeting molecule. When a targeting molecule is also incorporated into the vesicle, the vesicle will bypass the RES and go directly to the intended area.

If no targeting molecule is incorporated into the vesicle surface, the vesicle will circulate in the blood and when manufactured with a leaking membrane surface according to known techniques in the art, will release the contained cargo over an extended period of time for the benefit of medication at a continued regulated rate.

What is claimed is:

1. A delivery system consisting essentially of a biochemical membrane containing a drug, hormone, diagnostic or nutritional material covered with sialic acid residues such that the membrane is shielded from the RES thereby providing a coating that masks the surface membrane from recognition by the scavenging cells of the body.

2. The surface of the membrane in claim 1 which has an amphiphilic coating including N-acetylneuraminic acid.

3. A liposome having a core with at least one entrapped drug, hormone, diagnostic or nutritional material and the surface thereof masked from recognition by the reticuloendothelial system of the living body by having embedded in said surface the lipophilic portion of an amphiphilic coating which includes N-acetylneuraminic acid, the hydrophilic portion extending therefrom and substantially coating the surface.

4. The method of making a liposome carrier of drug, hormone, diagnostic or nutritional material masked from recognition by the scavenging cells of a living animal comprising the provision of an amphiphilic coating which includes N-acetylneuraminic acid and incorporating such coating into the manufacture of a liposome by known techniques.

* * * * *

UNITED STATES PATENT AND TRADEMARK OFFICE
CERTIFICATE OF CORRECTION

PATENT NO. : 4,501,728
DATED : February 26, 1985
INVENTOR(S) : W. Blair Geho

It is certified that error appears in the above-identified patent and that said Letters Patent are hereby corrected as shown below:

Column 4, line 9, insert the symbol " ∨ " in the quotation marks.

Claim 1, line 6, after "recognition" insert --and removed--.
Claim 1, line 6, after "scavenging" insert --RES--.

Signed and Sealed this

Thirtieth Day of July 1985

[SEAL]

Attest:

DONALD J. QUIGG

*Attesting Officer*  *Acting Commissioner of Patents and Trademarks*